United States Patent
DeRosa et al.

(10) Patent No.: US 10,883,075 B2
(45) Date of Patent: Jan. 5, 2021

(54) POLYMER SURFACES FOR CELL GROWTH

(71) Applicant: CORNING INCORPORATED, Corning, NY (US)

(72) Inventors: Michael Edward DeRosa, Painted Post, NY (US); Stephen Benedict Rimsa, Westford, MA (US); Kerry Elizabeth Robinson-Thompson, Burlington, MA (US); Kevin Andrew Vasilakos, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 277 days.

(21) Appl. No.: 15/328,805

(22) PCT Filed: Jul. 24, 2015

(86) PCT No.: PCT/US2015/041934
§ 371 (c)(1),
(2) Date: Jan. 24, 2017

(87) PCT Pub. No.: WO2016/014915
PCT Pub. Date: Jan. 28, 2016

(65) Prior Publication Data
US 2017/0211030 A1 Jul. 27, 2017

Related U.S. Application Data

(60) Provisional application No. 62/028,855, filed on Jul. 25, 2014, provisional application No. 62/028,857, filed on Jul. 25, 2014.

(51) Int. Cl.
*C12M 3/00* (2006.01)
*C12M 1/00* (2006.01)
(Continued)

(52) U.S. Cl.
CPC ............ *C12M 23/20* (2013.01); *C12M 23/04* (2013.01); *C12M 23/08* (2013.01); *C12M 23/10* (2013.01); *C12M 25/06* (2013.01)

(58) Field of Classification Search
CPC ...... C12M 23/06; C12M 23/20; C12M 23/08; C12M 23/10; C12M 25/06
See application file for complete search history.

(56) References Cited

U.S. PATENT DOCUMENTS

| 3,174,941 A | 3/1965 | Ericks et al. |
| 4,588,099 A * | 5/1986 | Diez .................... B65D 51/20 |
| | | 215/232 |

(Continued)

FOREIGN PATENT DOCUMENTS

WO      2005018905 A1    3/2005

OTHER PUBLICATIONS

Data Sheet for Trycite. Transcendia. 2016. (Year: 2016).*
(Continued)

*Primary Examiner* — Kara B Boyle
(74) *Attorney, Agent, or Firm* — F. Brock Riggs

(57) ABSTRACT

A cell culture article comprises virgin polystyrene disposed over at least a portion of a surface of an article main body. The article main body may be formed from polyethylene terephthalate (PET) such as reground or recycled polyethylene terephthalate. Methods of making such a cell culture article include applying a composition to a surface of an article main body, where the composition comprises virgin polystyrene having a thickness of 1 to 500 microns and the article main body is formed from glass, ceramic, metal or polymer.

12 Claims, 12 Drawing Sheets

(51) Int. Cl.
C12M 1/12 (2006.01)
C12M 1/24 (2006.01)
C12M 1/22 (2006.01)

(56) References Cited

U.S. PATENT DOCUMENTS

| | | |
|---|---|---|
| 2005/0186372 A1 | 8/2005 | Shah et al. |
| 2006/0063195 A1 | 3/2006 | Short et al. |
| 2006/0281172 A1 | 12/2006 | Kuwabara et al. |
| 2007/0166819 A1 | 7/2007 | Ghosh et al. |
| 2009/0246864 A1 | 10/2009 | Szlosek |
| 2012/0156773 A1* | 6/2012 | Smith ................ C12N 5/0068 435/350 |
| 2013/0052735 A1 | 2/2013 | DeRosa et al. |
| 2013/0071918 A1 | 3/2013 | Kim et al. |
| 2013/0210140 A1 | 8/2013 | Burns et al. |

OTHER PUBLICATIONS

International Searching Authority; Patent Cooperation Treaty; International Search Report and Written Opinion; International Application No. PCT/US2015/041934; dated Oct. 26, 2015; pp. 1-10.

* cited by examiner

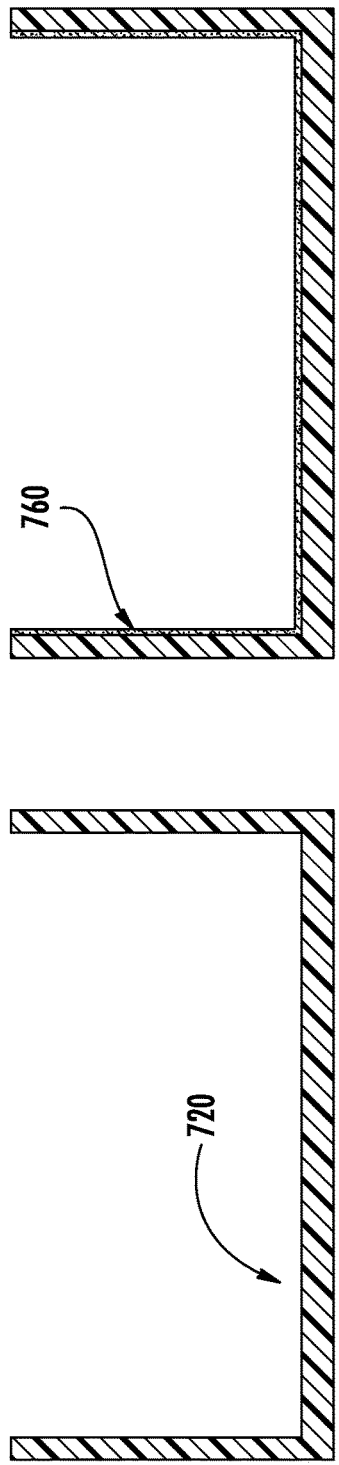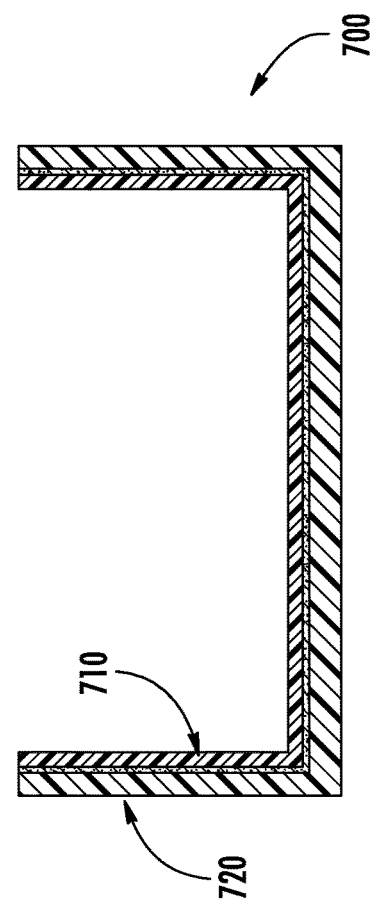

POLYMER SURFACES FOR CELL GROWTH

CROSS-REFERENCE TO RELATED APPLICATIONS

This application claims the benefit of priority under 35 U.S.C. § 371 of International Application No. PCT/US2015/041934, filed on Jul. 24, 2015, which claims the benefit of priority under 35 U.S.C. § 119 of U.S. Provisional Application Ser. No. 62/028,855 filed on Jul. 25, 2014, and U.S. Provisional Application Ser. No. 62/028,857, filed on Jul. 25, 2014, the contents of which are relied upon and incorporated herein by reference in their entirety.

BACKGROUND

Field

The present disclosure relates generally to methods for manufacturing labware, and more specifically to methods for forming surfaces for cell growth as well as the resulting surfaces.

Technical Background

The cultivation of living cells is a key component to, among other things, the drug discovery process. Cell culture articles used for such purposes include roller bottles, flasks, dishes, multi-well plates, cell harvesting units, etc. These items are typically molded from polymers to provide a cell culture surface for cell attachment and growth.

Cell culture articles may be formed from mechanically durable polymers such as polystyrene. There is a need, however, to decrease the cost associated with such articles. One approach to cost reduction involves decreasing the amount of material used to form a given part, i.e., via the formation of thinner articles. Toward this end, thin polystyrene shapes can be formed by injection molding, but are intrinsically size limited due to thickness and the flow characteristics of the polystyrene source resin. Coining and injection compression molding can be used to form incrementally thinner and mechanically robust polystyrene shapes, but such methods are associated with high capital costs and are also limited by the properties of the polystyrene resin. In view of the foregoing, it would be advantageous to develop more economical manufacturing methods to form cell culture articles.

BRIEF SUMMARY

In accordance with embodiments of the present disclosure, a cell culture article comprises a main body having a surface formed from polystyrene. The polystyrene presents an effective cell culture surface while a less costly (e.g., reground or recycled) resin is used to form the main body. Surfaces not normally suited to cell growth may be converted to support cell growth via application of the polystyrene coating. The polystyrene may be applied to the article only where needed.

A method of making a cell culture article comprises forming a polystyrene surface coating on at least a portion of the article main body. In embodiments, the polystyrene surface coating is derivable from a polystyrene-containing solution. Example solution compositions include 2-10 wt. % polystyrene dissolved in a ketone or ester solvent, which may be dip-coated, spin-coated, etc. to form the polystyrene coating.

A further method of forming a cell culture article comprises applying an overmolding composition to a surface of an article main body, wherein the overmolding composition comprises virgin polystyrene. The article main body may be formed from glass, ceramic, metal or polymer.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which:

FIG. 12A-12C are a schematic of a lamination process for forming a cell culture article;

DETAILED DESCRIPTION

Figure 1:
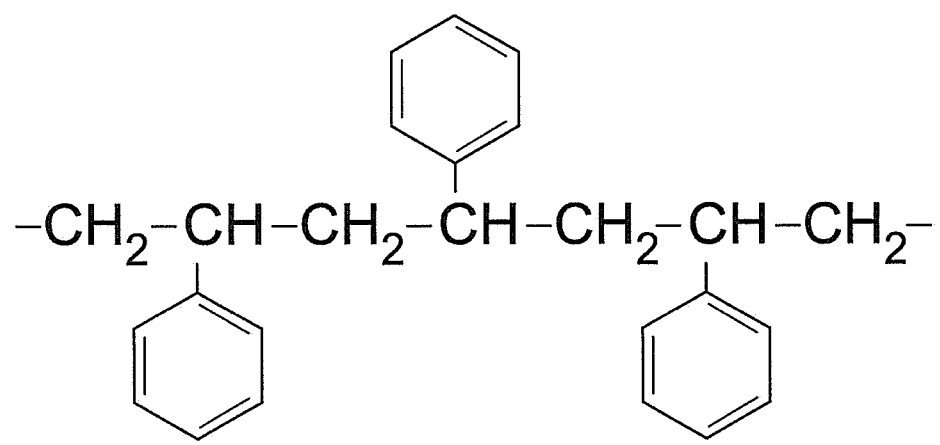
FIG. 1 is a diagram showing the molecular structure of polystyrene.

Reference will now be made in greater detail to various embodiments of the subject matter of the present disclosure, some embodiments of which are illustrated in the accompanying drawings. The same reference numerals will be used throughout the drawings to refer to the same or similar parts.

Disclosed is an economical technology for manufacturing labware suitable for use in tissue culture applications. In embodiments, a cell culture article comprises a main body that includes a virgin polystyrene (PS) surface. The article may comprise cell culture vessels such as Petri dishes and other laboratory containers such as flasks, tubes, bottles, multi-well plates, and cell-harvesting units.

In embodiments, a cell culture article comprises a main body that includes a coated or laminated surface layer of virgin polystyrene (PS). The article is comprised mostly of a low cost material and only a thin layer of polystyrene is used in locations where active cell culture is to take place.

By providing a virgin polystyrene-containing cell culture surface, the article main body may be molded from a lower cost material than polystyrene, such as reground or recycled polymers.

In embodiments, the cell culture article comprises a 1 to 500 micron thick polystyrene layer formed over reclaimed or recycled PET (i.e., RPET). In embodiments, the article is configured such that the main body comprises at least 50% by volume of the article. In embodiments, the cell culture article comprises a virgin polystyrene coating formed over reclaimed or recycled PET (i.e., RPET).

The disclosed technology can decrease material costs by 25-50% while obviating the need to form thinner labware to achieve such a cost reduction. As used herein, a "virgin" polymer such as virgin polystyrene is newly-manufactured, not reground or recycled. As used herein, a layer that is "formed over" or "disposed over" a substrate may be in direct physical contact with the substrate or physically separated from the substrate by one or more intervening layers.

The article may comprise cell culture vessels such as Petri dishes and other laboratory containers such as flasks, tubes, bottles, multi-well plates, and cell-harvesting units. The main body of the cell culture article may be formed from a glass, ceramic, metal or polymer. Polymeric main bodies, for example, may be formed using thermoplastic or thermosetting resin materials. Suitable thermoplastics include polystyrene (PS), acrylonitrile butadiene styrene, polycarbonate (PC), polyethylene (PE), polyethylene terephthalate (PET), polymethyl methacrylate (PMMA), polypropylene, cyclic olefin copolymers (COCs), transparent co-polymers such as styrene maleic anhydride, as well as combinations thereof. In embodiments, the article main body does not include polystyrene.

The article main body may be formed using injection molding or blow molding processes. An article main body formed from a polymer may optionally be fiber reinforced. By using a low-cost recycled thermoplastic for the bulk of the article, the form factor (including wall thickness) of the article main body can be both economical and mechanically robust.

As an example, a cell culture article comprising a virgin polystyrene cell growth surface and a main body formed from PET or polycarbonate may exhibit enhanced mechanical properties including improved impact resistance relative to conventional labware, which could reduce the propensity for breakage during shipping. In a further example, a composite of cyclic olefin co-polymer and polystyrene may exhibit enhanced optical properties such as relatively low background fluorescence.

Because the PS effectively seals the surface of the article main body, the latter may be formed using conventional stereo lithography (SLA), which otherwise is an unsuitable manufacturing method for cell culture article due to the cytotoxicity of the attendant UV-irradiated polymers. In a similar vein, the article main body may be formed from a material ineffective or otherwise unsuitable for cell growth.

In embodiments, the surface is formed from a polystyrene-containing solution. In embodiments, the surface layer includes a laminated thin film of virgin polystyrene. Polystyrene (poly(1-phenylethylene)) is a synthetic aromatic polymer. Polystyrene is formed when styrene monomers interconnect. During the polymerization, the carbon-carbon pi bond in the vinyl group of the styrene monomer is broken and a new carbon-carbon sigma (single) bond is formed, attaching another styrene monomer to the chain. Along the carbon backbone of a polystyrene chain, alternating carbon centers are attached to a phenyl group. The structure of polystyrene, which can be represented as $(C_8H_8)_n$, is shown in FIG. 1. As an amorphous thermoplastic polymer, polystyrene (PS) exists in a solid (glassy) state at room temperature but flows if heated above its glass transition temperature (100° C.).

The polystyrene used to form the surface layer may be a general purpose, high molecular weight crystal polystyrene such as, for example BASF PS 158K, which is marketed by INEOS, Rolle, Switzerland. The polystyrene weight average molecular weight (Mw) may range from 250,000 to 500,000, e.g., 250,000, 300,000, 350,000, 400,000, 450,000 or 500,000, including ranges between any of the foregoing.

In embodiments, a surface suitable for cell growth is prepared via the application of a coating comprising crystalline (syndiotactic) polystyrene polymer. The coating may be formed via deposition of an organic, polystyrene-containing solution. The solution may comprise 2-10 wt. % polystyrene, for example 2, 4, 6, 8, or 10 wt. % polystyrene, including ranges between any of the foregoing, dissolved in a solvent.

Suitable solvents readily dissolve polystyrene but should be poor solvents for the substrate (i.e., article main body). Example solvents include various ketones and esters such as, for example, acetone, methyl ethyl ketone (MEK), methyl isopropyl ketone (MIPK), methyl isobutyl ketone (MIBK), isobutyl isobutyrate (IBIB), methyl n-amyl ketone (MAK), methyl isoamyl ketone (MIAK), as well as mixtures thereof.

Example methods include forming a polystyrene-containing solution by dissolving a solid source of polystyrene in a solvent, and applying the solution to a surface of the article main body, e.g., via dip coating, spin coating, spray coating, gravure rolling, slot coating or wire-wound metering rod coating. The polystyrene coating is formed in situ on the article main body. In other words, the coating is generated as the coating composition is deposited onto a surface. Thus, an article main body is provided (formed first) and then a polystyrene coating is formed over a surface of the article main body. Without wishing to be bound by theory, it is believed that adhesion between the polystyrene and the article main body is promoted by a degree of etching by the ketone or ester solvent(s) of the article main body.

In embodiments, the polystyrene solution is applied directly to a surface of the article main body. In alternate embodiments, the polystyrene solution is applied to an intermediate coating or layer that has been formed over a surface of the article main body. The intermediate coating or layer may comprise a coupling agent, for example, which enhances the bond strength (adhesion) between the polystyrene coating and the article main body. An example coupling agent is the tri-block co-polymer Kraton® D1111, which is based on styrene and isoprene and has a polystyrene content of about 22%. An adhesion-promoting material can be applied to a surface of the article main body as an aqueous or organic solution of the adhesive. In embodiments, an adhesion-promoting surface treatment comprises applying an adhesive liquid or bonding film to one or both of the article main body and the laminate.

In further embodiments, a surface suitable for cell growth is prepared via plasma polymerization of a polystyrene coating directly onto a surface of the article main body. Plasma polymerization of polystyrene is accomplished by placing an article main body in a CVD vacuum chamber followed by the introduction of polystyrene monomer into the chamber. The monomer may be preheated and is introduced into the chamber in a gaseous state. A polystyrene coating is formed on a surface of the article by initiating a plasma suitable for free radical polymerization, for example using RF energy at a microwave frequency.

In further embodiments, a surface suitable for cell growth is prepared via the application of a layer comprising amorphous (atactic) polystyrene polymer. A cell culture article may be formed via lamination of a polystyrene layer over a surface of the main body. The laminate can be applied by various thermoplastic processing methods such as overmolding, thermoforming, in-mold labeling, or coining.

Overmolding is an injection molding process where one material (e.g., polystyrene) is molded onto a second material (e.g., polyethylene terephthalate). In an example process, a pre-molded insert of one material is placed into a mold and the other material is shot directly over the insert. While various examples disclosed herein are described in the context of an overmolded polystyrene layer, i.e., an article formed by providing a pre-molded main body and overmolding a virgin polystyrene layer onto a surface of the main body, it will be appreciated that a cell culture article may be formed by overmolding a material onto a polystyrene pre-form. For instance, an example cell culture article is formed by over molding polystyrene (Tg~105° C.) onto a pre-form of PET ($T_m$~250-260° C.). In a further example, a cell culture article is formed by overmolding polyethylene ($T_m$~120-180° C.) onto a pre-form of polystyrene.

In embodiments, the overmolding material is melted and injected into a closed mold comprising the article main body to form the cell culture article. After cooling, the article is removed from the mold.

In embodiments, the polystyrene layer is laminated directly to a surface of the article main body. In alternate embodiments, the polystyrene layer is applied to an intermediate coating or layer that has been formed over a surface of the article main body. The intermediate coating or layer may comprise a thermal bonding film or adhesive coating, for example, which enhances the bond strength and inhibit delamination between the polystyrene layer and the article main body. Further suitable adhesion-promoting materials are listed in Table 1. An adhesion-promoting material can be applied to a surface of the article main body as an aqueous or organic solution of the adhesive. In embodiments, an adhesion-promoting surface treatment comprises applying an adhesive liquid or bonding film to one or both of the article main body and the laminate. An adhesion-promoting material can comprise a re-meltable adhesive material.

In embodiments where an adhesion-promoting material is used, a cell culture article comprises a layer of the adhesion-promoting material at the interface between the polystyrene layer and the article main body. The adhesion-promoting material layer thickness can range from 1 to 100 microns, e.g., 1, 2, 5, 10, 20, 50 or 100 microns, including ranges between any two of the foregoing values.

Optionally, a surface treatment step such as oxygen, air or nitrogen plasma can be used to improve adhesion between the polystyrene and the article main body. Plasma treatment of the article main body may be conducted in lieu of the application of an adhesive liquid or bonding film or, in embodiments, plasma treatment of the article main body may be conducted as a surface-conditioning step prior to the application of an adhesive liquid or bonding film.

In further embodiments, apertures can be fashioned into the surface of the main body such that the polystyrene layer, when overmolded, flows at least partially into the apertures resulting in the formation of mechanical rivets that lock the two layers together.

It is within the ability of one skilled in the art to determine which portion(s) of the article to coat or laminate with polystyrene, which may include, for example, consideration of the method of forming the coating and the intended use of the cell culture article, such as the type of cells to be grown and/or the nature of the assay. In various embodiments, for example, the polystyrene coating or layer may cover at least a portion of an interior surface of a dish, flask, test tube, or roller bottle. The polystyrene may be formed over a portion of the article main body or over substantially all of the main body. In the example of a Petri dish, the polystyrene can be formed as an inner liner of the dish.

In further embodiments, the polystyrene may manifest as a patterned coating or layer, such as a ribbed pattern, diamond pattern, cross-hatched pattern, dot pattern, dimple pattern, zig-zag pattern, spiral pattern, circular pattern, square pattern, triangular pattern, hexagonal pattern, rectangular pattern, and the like.

The polystyrene coating, after it is applied, may be air dried, though drying may be accelerated using an oven or a vacuum chamber. The polystyrene coating may be dried at a temperature ranging from about 25° C. to 100° C. In embodiments, the evaporation rate of the solvent should be less than 40% of the evaporation rate of n-butyl acetate to avoid the formation of haze or an opaque appearance due to the condensation of moisture on the polystyrene coating.

Where applied, the average coating thickness of the polystyrene may range from about 2 to 50 microns, e.g., 2, 5, 10, 20, 30, 40 or 50 microns, including ranges between any of the foregoing. In various embodiments, the polystyrene coating may be uniform in thickness and in other embodiments it may not be uniform in thickness. The polystyrene coating may have a density of 1.02 to 1.05 g/cm$^3$.

In embodiments, the cell culture article is configured such that the article main body comprises at least 50% by volume of the article. For example, in embodiments, the article main body comprises 50, 55, 60, 65, 70, 75, 80, 85, 90 or 95 vol. % of the article, including ranges between any two of the foregoing values.

Where applied, the average laminate thickness of the polystyrene may range from about 1 to 500 microns, e.g., 1, 2, 5, 10, 20, 50, 100, 200, 300, 400 or 500 microns, including ranges between any of the foregoing. In various embodiments, the polystyrene layer may be uniform in thickness and in other embodiments it may not be uniform in thickness. The polystyrene coating may have a density of 1.02 to 1.05 g/cm$^3$.

As-deposited, un-modified (untreated) polystyrene surfaces are hydrophobic in nature and bind cells and biomolecules merely through passive interactions. This type of surface is referred to as medium binding and is primarily suitable for the immobilization of large molecules, such as antibodies, which have large hydrophobic regions that can interact with the surface (FIG. 1). Due to the large surface area needed to immobilize biomolecules in this manner, binding capacities are typically low: 100-200 ng IgG/cm$^2$.

In many cell growth applications, the growth container or culture surface may be surface treated in order to increase its hydrophilic character (wettability) and enhance the kinetics for effective cell attachment. Surface treatment may take the form of a further surface coating, but typically involves the use of directed energy to generate chemical groups on the polymer surface. Examples of directed energy include atmospheric corona discharge, radio frequency (RF) vacuum plasma treatment, and DC glow discharge.

Surface chemical groups will have an affinity for water or otherwise exhibit sufficient polarity to permit stable adsorption of another polar group. Chemical groups include amines, amides, carbonyls, carboxylates, esters, hydroxyls, sulfhydryls, and the like. These functional groups lead to an increase in surface oxygen and/or hydrophilicity, which can enhance cell growth.

Figure 2:
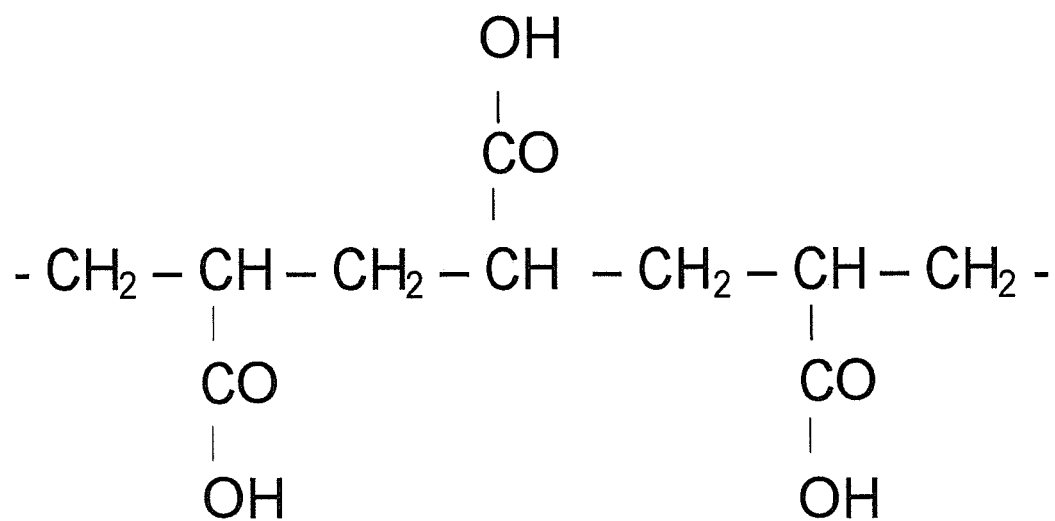
FIG. 2 is a diagram showing the molecular structure of carboxylated polystyrene.

The free surface of the polystyrene coating may be modified to a high-binding state, e.g., through the use of radiation. The radiation effectively incorporates carboxylic acid on the accessible carbons of the "broken" benzene ring (FIG. 2). The resulting surface is primarily hydrophobic (but possesses both hydrophilic and hydrophobic characteristics) with intermittent carboxyl groups capable of ionic interactions with positively charged groups on biomolecules. The immobilization mechanism is passive adsorption through hydrophobic and ionic interactions. This is considered a general purpose surface capable of binding medium (>10 kDa) and large biomolecules that possess ionic groups and/or hydrophobic regions. Binding capacity is increased as compared to the medium binding surface to approximately 400-500 ng IgG/cm$^2$ because ionic interactions require that a smaller portion of the molecule be in contact with the surface to obtain stable immobilization.

Figures 3, 4:
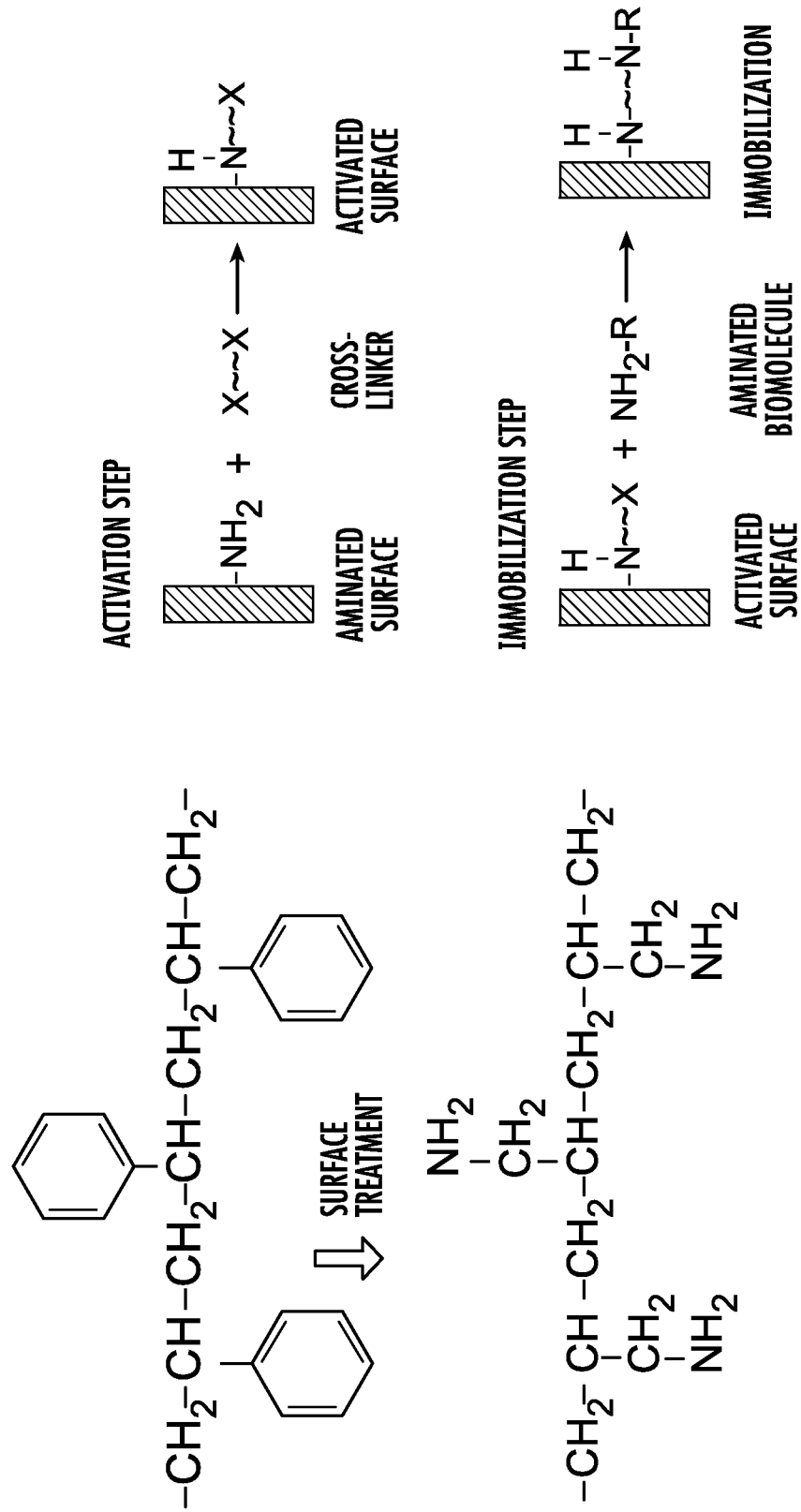
FIG. 3 is a diagram depicting the formation of an aminated polystyrene.
FIG. 4 illustrates an example 2-step process for biomolecule immobilization on an aminated polystyrene surface.

In further embodiments, the polystyrene coating can be modified to comprise positively-charged amine groups that replace the benzene ring at the surface (FIGS. 3 and 4). In FIG. 3, benzene groups have been replaced with amine groups to form an aminated PS surface. This type of surface lacks hydrophobic character and is ionic in nature. Using appropriate buffers and pH, this surface can be used to ionically couple to small negatively-charged biomolecules. The lack of hydrophobic areas on the surface precludes the immobilization of large, relatively hydrophobic molecules. This surface may be used with bi-functional crosslinkers (i.e., glutaraldehyde, carbodiimide, etc.) to covalently couple to functional groups (primary amines, thiols, and carboxyls) on biomolecules. Due to its hydrophilic nature and capability of covalent immobilization through the use of additional crosslinkers, the aminated surface can be used to immobilize molecules solubilized in detergents, such as Triton® X-100 and Tween 20.

Figure 5:
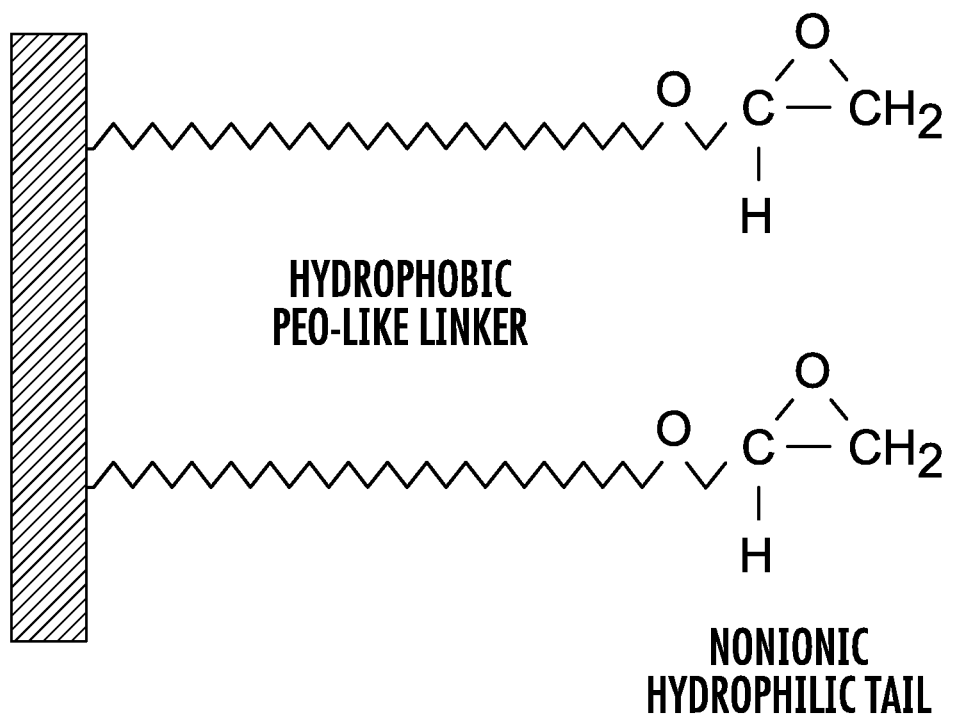
FIG. 5 is a diagram showing PEO chains immobilized on a polystyrene surface.

Some assays and procedures require a surface that is non-binding to cells because many proteins, enzymes in particular, become activated or inactivated upon attachment to a surface. Since proteins and other biomolecules passively adsorb to surfaces primarily through hydrophobic and ionic interactions, a nonionic, hydrophilic surface (polyethylene oxide [PEO]-like) minimizes molecular interactions and inhibits non-specific immobilization via these forces (FIG. 5).

The polystyrene coating or layer may be transparent or colored via the addition of colorants. In embodiments, an anthraquinine-based dye is added to the polystyrene to offset yellowing that occurs during sterilization. In embodiments, the article main body is transparent.

In embodiments, the cell culture article is transparent. As used herein, "transparent" means at least 80% transparency (e.g., at least 80, 82, 84, 86, 88, 90, 92, 94, 96, 98, 99 or 100% transparency) for a given wavelength or over a range of wavelengths. In embodiments, the cell culture article is transparent to visible light (i.e., over the wavelength range of 390 to 700 nm). In embodiments, the cell culture article is transparent to ultraviolet and/or near-infrared radiation (i.e., over the respective wavelength ranges of 100 to <390 nm and >700 to 2500 nm).

In embodiments, the cell culture article is characterized by low background fluorescence. Fluorescence is a form of absorbed energy that is reradiated at a lower energy, often as light. The amount of fluorescence (or lack thereof) from cell culture articles is a key factor in their implementation with, for example, analytical spectroscopy, polarization, and imaging, including point-of-care (POC) in vitro diagnostic tests, and other life-sciences analytics such as cellular flow cytometry.

The intensity of the background fluorescence of the cell culture article varies with the excitation and emission wavelengths used, but is preferably low over a wide range of wavelengths.

EXAMPLES

Figure 6:
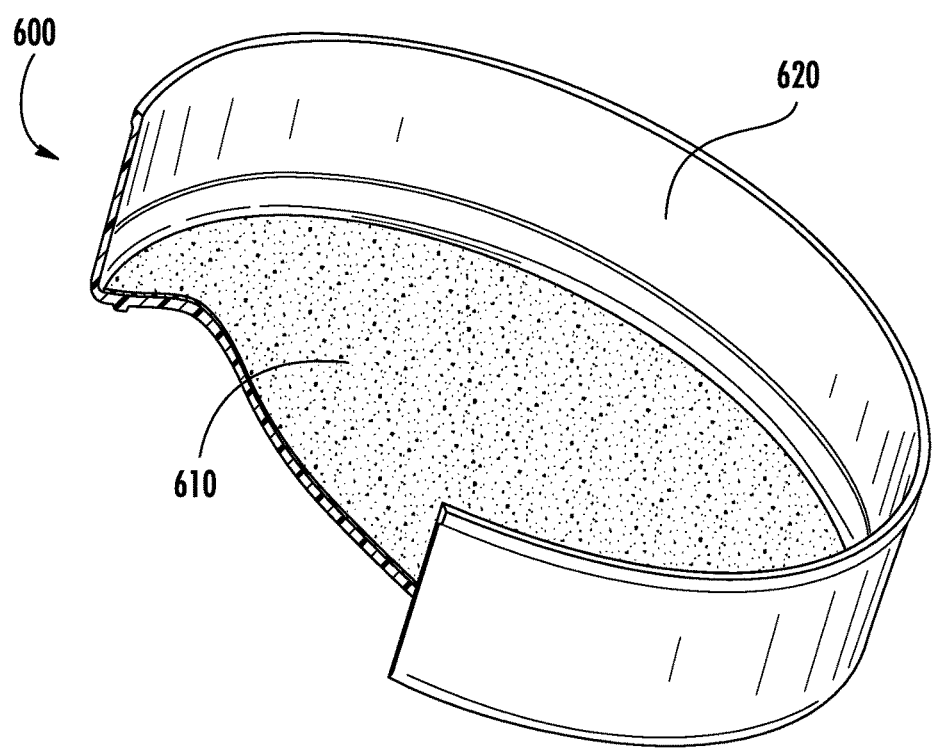
FIG. 6 is an illustration of a polyethylene terephthalate (PET) cell culture article with a polystyrene cell-growth surface.
Figure 7:
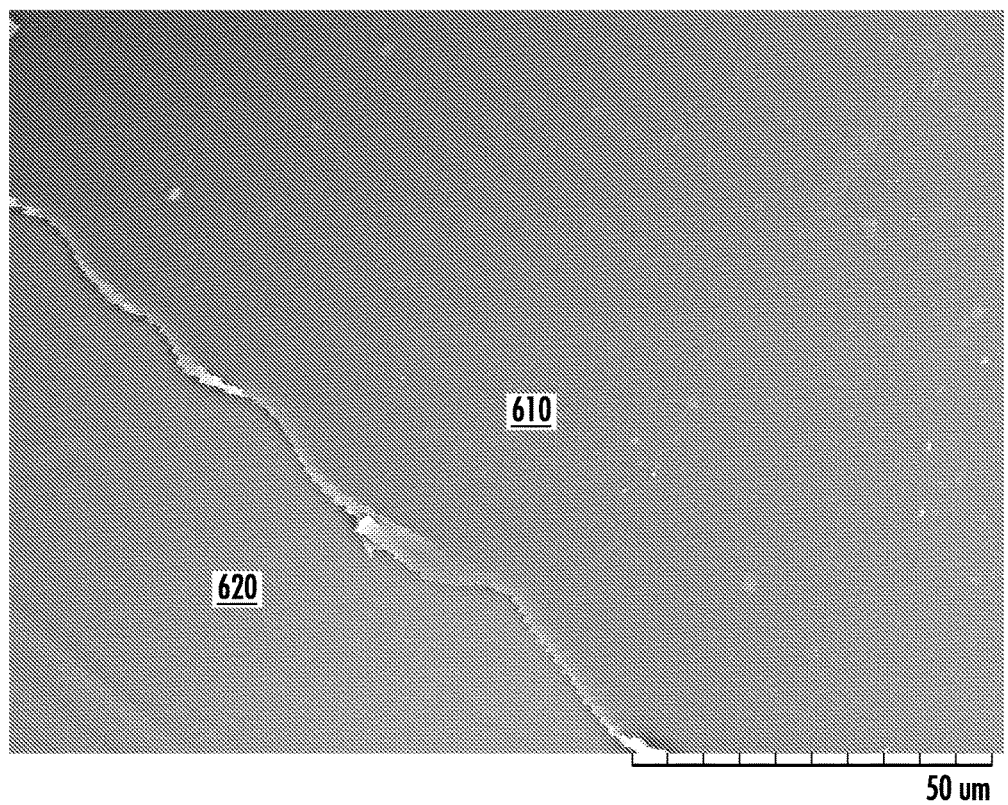
FIG. 7 is an SEM micrograph of a portion of a PET Petri dish coated with polystyrene.

Shown in FIG. 6 is a 100 mm tissue culture plate 600 fabricated from PET and comprising a polystyrene coating 610 applied to form a cell growth surface. FIG. 7 is a scanning electron microscope (SEM) micrograph showing the polystyrene coating 610 and an exposed portion of the PET main body 620.

The contact angles formed with water of a PET dish, PS-coated PET dish, and a 100% PS dish are summarized in Table 1. As seen with reference to Table 1, after coating with a PS solution, the contact angle of the PS-coated PET dish increases from 73.0° to 84.8°, and is greater than 99.5% of the contact angle of 100% PS (85.0°).

The PS-coated PET dish and the 100% PS dish were tissue culture (TC) treated and allowed to age following the TC treatment at 25° C. for 18 days. The TC treatment comprises exposing the dish to 100 W (50 mTorr) RF plasma for 10 seconds. The post-TC treatment contact angles were 34.0° and 38.8°, respectively.

TABLE 1

Contact angles of cell growth surfaces

| Surface Composition | Contact Angle | Contact Angle after TC treatment |
|---|---|---|
| 100% PET | 73.0° | |
| PS-coated PET | 84.8° | 34.0° |
| 100% Polystyrene | 85.0° | 38.8° |

Applicants have shown that PS-coated PET dishes possess a cell growth surface comparable to that of dishes formed from 100% injected molded polystyrene. Cell attachment and growth were evaluated for a PS-coated, TC-treated PET dish (coated 2× with a 5 wt. % PS solution in MIBK) as well as for TC-treated and non-TC-treated 100% PS dishes.

MRC-5 cells (ATCC cat #CCL-171, human lung fibroblast) were seeded on 100 mm dishes at ~22K cells/$cm^2$ in Eagle's minimal essential cell culture medium (EMEM) supplemented with 10% fetal bovine serum (FBS). Cells were incubated at 37° C./5% $CO_2$. Cell growth was visually examined 24 hours post-seeding. At 48 hours, cells were again visually examined. One dish of each surface was scanned with Essen Incucyte to measure confluence. Cells were harvested from each scanned dish and counted using a Beckman Coulter ViCell cell viability analyzer.

Figure 8:
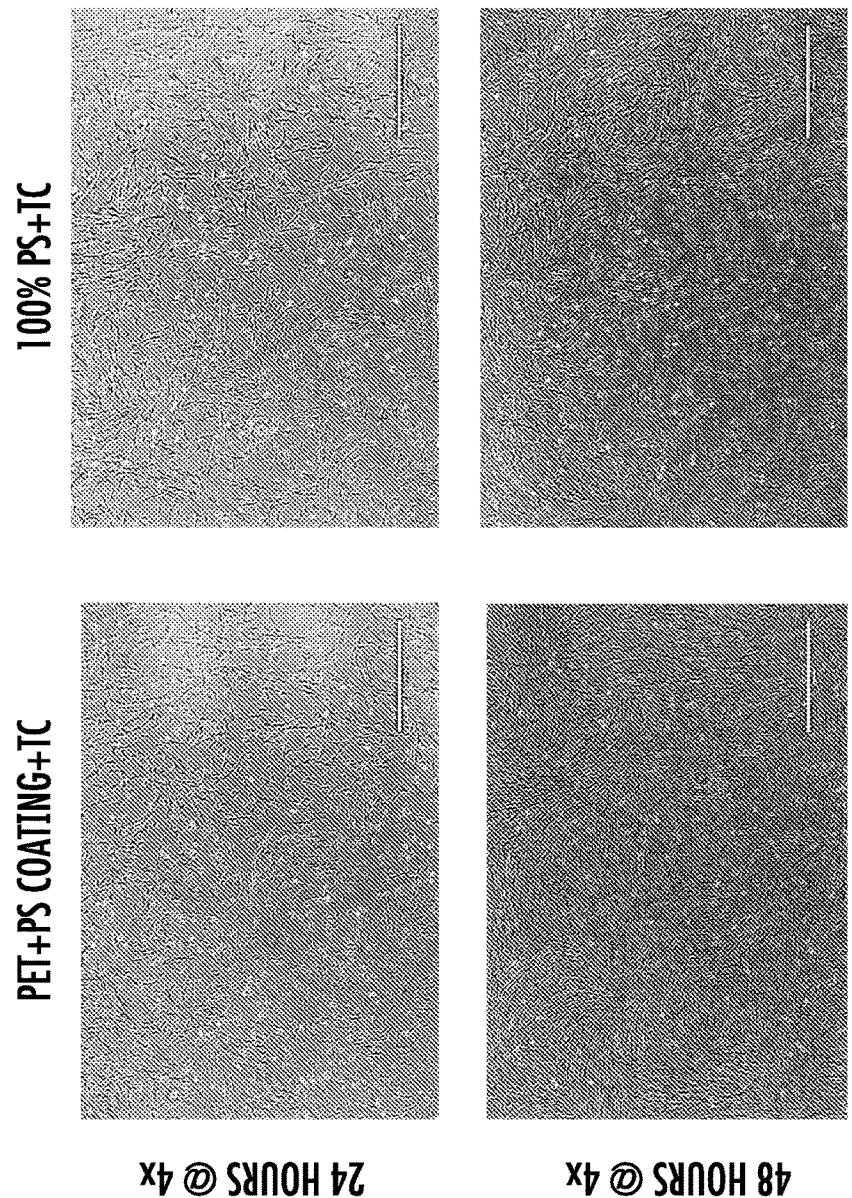
FIG. 8 is a series of optical micrographs evidencing comparable tissue cell growth on 100% PS dishes (comparative) and PS-coated PET dishes at incubation times of 24 and 48 hrs.

Optical micrographs showing cell morphology and distribution of MRC-5 cells on the TC-treated growth surfaces are depicted in FIG. 8 for the PS-coated PET dishes (left column) and the comparative 100% PS dishes (right column). At cell growth times of 24 hrs (top row) and 48 hrs (bottom row) the cell density for growth on the polystyrene surface coating was comparable.

Figure 9:
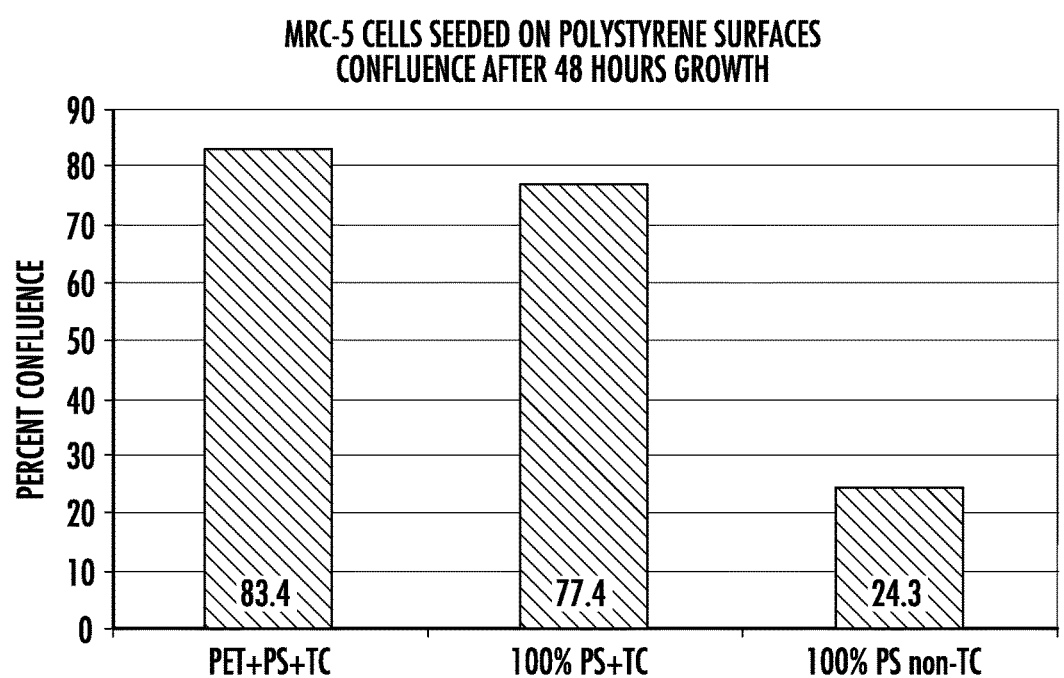
FIG. 9 is a plot showing percent confluence for different cell growth surfaces.
Figure 10:
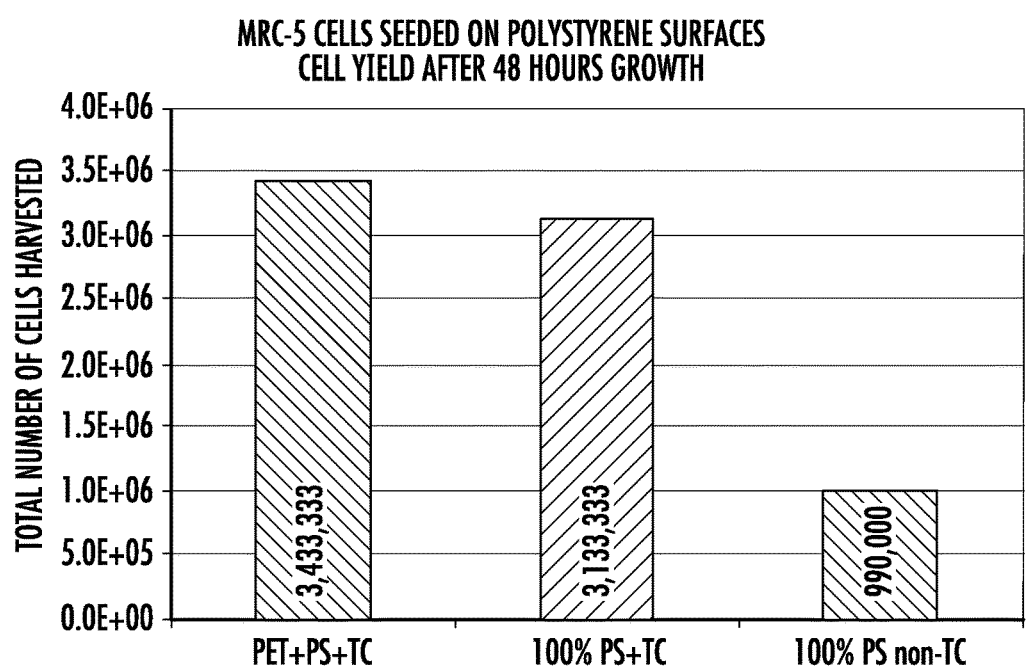
FIG. 10 is a plot showing cell yield for different cell growth surfaces.

Referring to FIGS. 9 and 10, which show confluence and cell yield data, respectively, it can be seen that the confluence for cells grown on the PS-coated, TC-treated PET dish was 8% greater than that for the TC-treated 100% PS dish, and the cell yield for cells grown on the PS-coated, TC-treated PET dish was 10% greater than that for the TC-treated 100% PS dish.

Figure 11B:
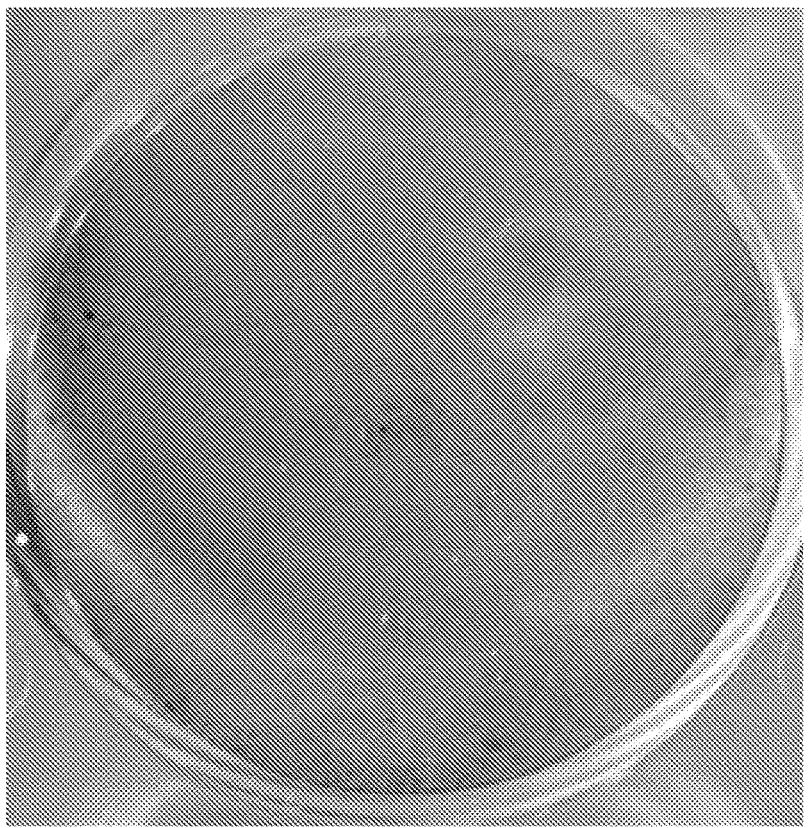
FIG. 11B is an optical micrograph of a comparative 100% PS dish.
Figure 11A:
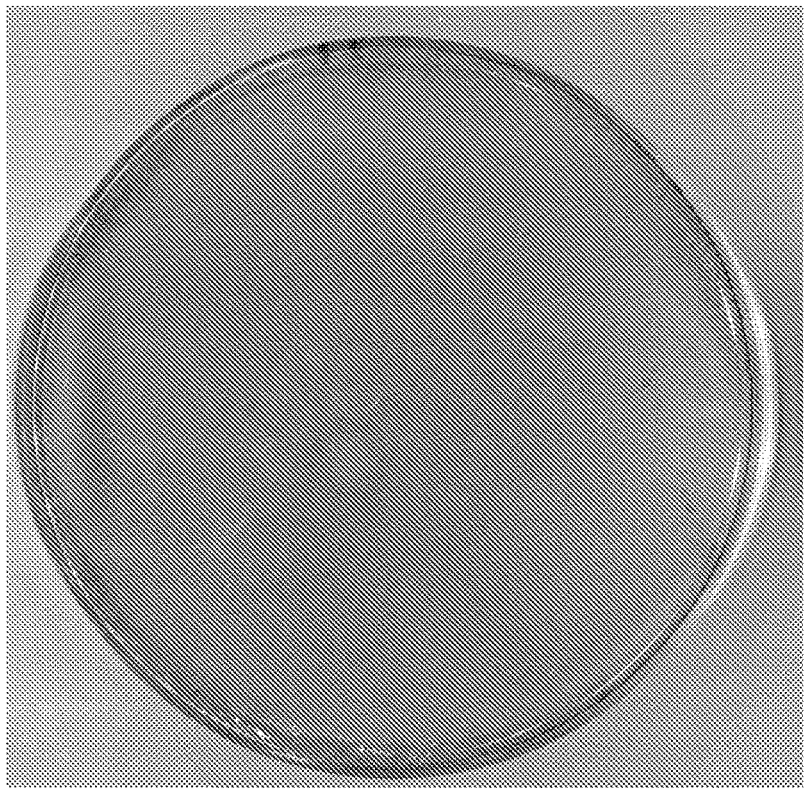
FIG. 11A is an optical micrograph of a PS-coated PET dish according to embodiments.

In a further experiment, MRC-5 cells were seeded at ~22K cells/$cm^2$ in EMEM/10% FBS. Cells were incubated at 37° C./5% $CO_2$ for 96 hours. Cells were fixed with paraformaldehyde (PFA) and stained with crystal violet. As seen in the optical micrographs of FIG. 11, the cell density and cell distribution on (A) a PS-coated, TC-treated PET dish was comparable to the cell density and distribution on (B) a TC-treated, 100% PS control plate.

FIGS. 12A-12C are a schematic of a lamination process for forming a composite article 700. An article main body 720 such as a Petri dish (shown in cross-section) formed from a recycled, transparent thermoplastic is optionally treated to form an adhesion-promoting layer 760. In the illustrated embodiment, a polystyrene layer 710 is overmolded to an inner surface of the main body. An example polystyrene layer material includes Trycite™ polystyrene films marketed by the Dow Chemical Company (Midland, Mich.).

Figure 13B:
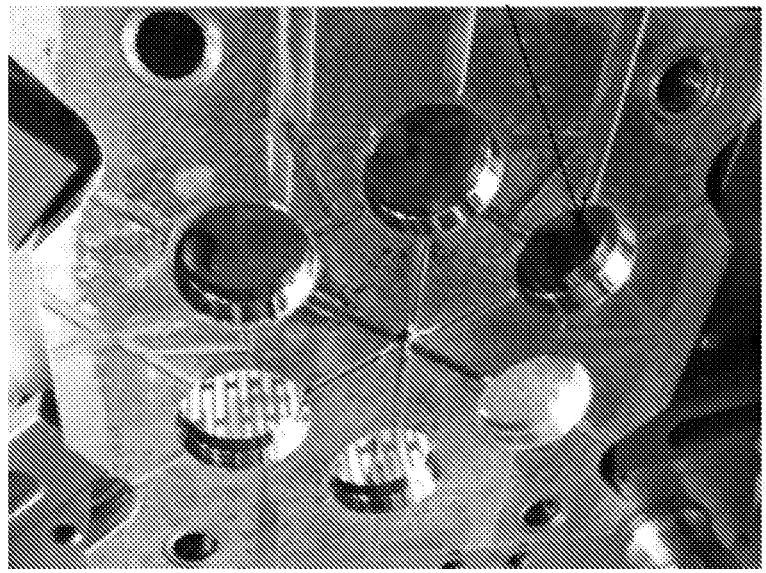
FIGS. 13A and 13B are photographs of a Petri dish mold used in various embodiments.
Figure 13A:

An Arburg Allrounder 370C injection molding machine using a six cavity, 5.5 cm diameter Petri dish mold was employed to form two-part, transparent thermoplastic Petri dishes. Three cavities are used to form the dish lids, and three cavities are used to form the dish bottoms. Photographs of the opposing halves of the six cavity mold are shown in FIGS. 13A and 13B.

Example 1 (Comparative)

As a comparative control, Styrolution® PS 1200 general purpose polystyrene was overmolded onto untreated 0.25 mm and 0.50 mm thick PET sheets. The PET was cut into 1.98 in diameter disks but otherwise used as-received. Process conditions for the molding are summarized in Table 2.

TABLE 2

Arburg injection molding process conditions.

| | | | |
|---|---|---|---|
| Mold temp - fixed half (A) | 140° F. | Dosage | 37 $cm^3$ |
| Mold temp - moving half (B) | 140° F. | Holding pressure base 1 | 900 bar |
| Zone 1 temperature | 220° C. | Holding pressure base 2 | 900 bar |
| Zone 2 temperature | 230° C. | Holding time | 3 sec |
| Zone 3 temperature | 240° C. | Injection flow | 40 $cm^3$/sec |
| Zone 4 temperature | 250° C. | Switch over point | 3 |
| Zone 5 temperature | 260° C. | Molding cooling | 15 sec |

Example 2—Plasma Pre-Treatment

According to one embodiment, PS-to-PET adhesion was improved using a plasma pre-treatment of the PET. Prior to overmolding as in Example 1, the PET disks were exposed to a 200 W oxygen plasma for 5 min.

Example 3—Plasma Pre-Treatment and Adhesive Primer

According to a further embodiment, PS-to-PET adhesion was improved by treating the plasma-treated PET of Example 2 with an adhesive primer (e.g., Kraton® D-1111 dissolved in MIBK). The treated disc was then placed into the bottom of the mold cavity and overmolded with polystyrene.

Figure 14C:
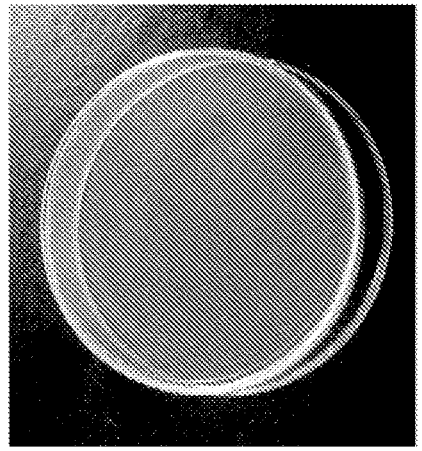
FIG. 14A-C is a series of optical micrographs of injection molded Petri dishes manufactured using different surface pre-treatments.
Figure 14B:
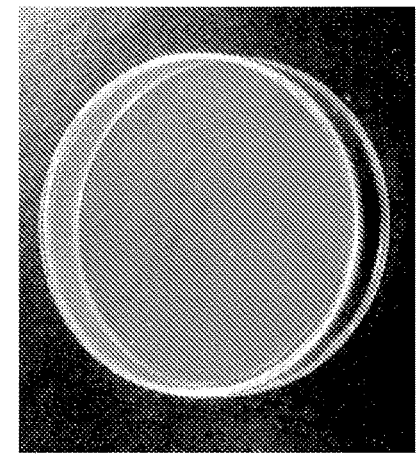
Figure 14A:
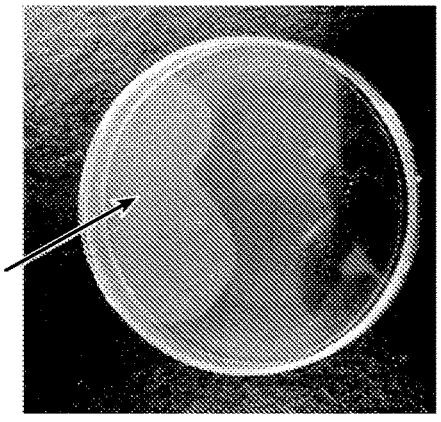

FIG. 14A-C is a series of optical micrographs showing the completed test structures (10 mil thick PET) for Examples 1-3. As seen with reference to FIG. 14A, absent plasma treatment of the PET surface or the incorporation of an adhesion-promoting layer at the interface, the PS-to-PET bonding was weak and delamination was evident. In contrast, with reference to FIGS. 14B and 14C respectively, no delamination was evident when the PET surface was conditioned prior to lamination using oxygen plasma (200 W for 5 min), or pre-treated by applying an adhesive primer to the PET surface.

Example 4—Bonding Agents Pre-Treatment

A 10 mil thick piece of PET sheet stock was cut into 100 mm diameter disks. Using a Meyer rod, one side of each disk was coated with a 1.2 mil thick wet layer of an adhesive bonding solution. A total of 6 different bonding solutions were tested to assess their effect on adhesion.

The treated disk was attached to the mold's core face using a static bar with the untreated PET surface in contact with the mold. Virgin polystyrene was molded over the adhesive-treated surface to form the final part. A summary of the bonding agents is listed in Table 3.

Relative adhesion of the PS to the PET dish bottom was determined by cracking the test dish in half With the exception of the Tykote 6152 treatment, all of the produced laminates exhibited good-to-excellent adhesion.

TABLE 3

Adhesion-promoting agents.

| Name | Description | Formulation |
|---|---|---|
| Kraton ® D-1111 | styrene-isoprene-styrene linear tri-block co-polymer | 15 & 20 wt. % solution in MIBK |
| Rovene ® 4019 | carboxylated styrene | 53% aqueous solution |

TABLE 3-continued

Adhesion-promoting agents.

| Name | Description | Formulation |
|---|---|---|
| Tykote ® 6152 | butadiene styrene-acrylic emulsion | 46% aqueous solution |
| Cattie Adhesives 8437 | polyurethane dispersion | 36% aqueous solution |
| Cattie Adhesives 8258 | carboxylated acrylic dispersion | 58% aqueous solution |
| Cattie Adhesives 8116 | vinyl acetate-ethylene co-polymer | 70% aqueous solution |

As used herein, the singular forms "a," "an" and "the" include plural referents unless the context clearly dictates otherwise. Thus, for example, reference to a "ketone solvent" includes examples having two or more such "ketone solvents" unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a surface coating comprising polystyrene include embodiments where a surface coating consists of polystyrene and embodiments where a surface coating consists essentially of polystyrene.

It will be apparent to those skilled in the art that various modifications and variations can be made to the present invention without departing from the spirit and scope of the invention. Since modifications, combinations, sub-combinations and variations of the disclosed embodiments incorporating the spirit and substance of the invention may occur to persons skilled in the art, the invention should be construed to include everything within the scope of the appended claims and their equivalents.

We claim:

1. A cell culture article comprising:
   a main body;
   a virgin polystyrene coating disposed over at least a portion of a surface of the main body and formed in situ on the main body from a polystyrene-containing solution deposited on the main body; and
   an adhesion-promoting material layer disposed between the main body and the polystyrene coating,
   wherein the main body is formed from glass, ceramic, metal or polymer and the polystyrene coating has a thickness of 2 to 50 microns, and
   wherein the polystyrene coating has a density of 1.02 g/cm$^3$ to 1.05 g/cm$^3$.

2. The cell culture article of claim 1, wherein the article is selected from the group consisting of a dish, flask, tube, bottle and plate.

3. The cell culture article of claim 1, wherein the main body comprises a polymer selected from the group consisting of acrylonitrile butadiene styrene, polycarbonate, polyethylene, polyethylene terephthalate, polymethyl methacrylate, polypropylene, a cyclic olefin co-polymer, styrene maleic anhydride, and combinations thereof.

4. The cell culture article of claim 1, wherein the main body comprises polyethylene terephthalate.

5. The cell culture article of claim 1, wherein the main body consists essentially of reground or recycled polyethylene terephthalate.

6. The cell culture article of claim 1, wherein the polystyrene coating is disposed over a portion of the main body.

7. The cell culture article of claim 1, wherein the polystyrene coating weight average molecular weight ranges from 250,000 to 500,000.

8. The cell culture article of claim 1, wherein the polystyrene coating comprises crystalline polystyrene.

9. The cell culture article of claim 1, wherein the cell culture article is transparent.

10. A cell culture article comprising:
    a dish, flask, tube, bottle or plate having a main body; and
    a virgin polystyrene coating disposed over at least a portion of a surface of the main body and formed in situ on the main body from a polystyrene-containing solution deposited on the main body; and
    an adhesion-promoting material layer disposed between the main body and the polystyrene coating,
    wherein the main body consists essentially of reground or recycled polyethylene terephthalate and the polystyrene has a thickness of 2 to 50 microns.

11. The cell culture article of claim 1, wherein the adhesion-promoting material layer has a thickness of from about 1 to about 100 microns.

12. The cell culture article of claim 1, wherein the polystyrene coating is a dip-coated coating, a spin-coated coating, a spray-coated coating, or a roll-coated coating.

* * * * *